United States Patent [19]

Roberts

[11] 4,272,629
[45] Jun. 9, 1981

[54] NOVEL PROSTAGLANDIN INTERMEDIATES

[75] Inventor: Stanley M. Roberts, Macclesfield, England

[73] Assignee: Allen & Hanburys Limited, London, England

[21] Appl. No.: 59,502

[22] Filed: Jul. 23, 1979

Related U.S. Application Data

[63] Continuation of Ser. No. 868,331, Jan. 10, 1978, abandoned.

[30] Foreign Application Priority Data

Jan. 11, 1977 [GB] United Kingdom .................. 952/77

[51] Int. Cl.$^3$ .................. C07D 303/06; C07D 493/10; C07D 497/10
[52] U.S. Cl. ......................................... 549/11; 549/4; 549/10; 549/31; 549/35; 260/340.7; 260/340.9R; 260/343.3 P; 260/348.54; 568/591; 260/346.22
[58] Field of Search ........ 260/327 M, 340.7, 340.9 R, 260/348.54; 549/10, 11, 35, 31; 568/591

[56] References Cited

U.S. PATENT DOCUMENTS

| 3,932,463 | 1/1976 | Schaub et al. |
| 3,966,815 | 6/1976 | Freed et al. |

FOREIGN PATENT DOCUMENTS

| 848992 | 6/1977 | Belgium .................................. 260/468 |
| 2800929 | 7/1978 | Fed. Rep. of Germany ............. 549/10 |

OTHER PUBLICATIONS

Newton et al., Chem. Abst., vol. 90, abst. 54517a, (1979).
Newton et al., J. Chem. Soc. Chem. Commun., 1978, pp. 662–664.
Chapman et al., Chem. Abst., vol. 57, col. 2092i, (1962), (abst. of JACS infra).
Chapman et al., J. Am. Chem. Soc., vol. 84, pp. 1213 to 1219, (1962).
Grudzinski et al., Chem. Abst., vol. 84, abst. 4542k, (1976), (abst. of J. Chem. Soc., Perkin Tans. 1, 1975, pp. 1767–1773).
Allen and Hanburys Ltd., Chem. Abst., vol. 88, abst. 6400u, (1978), (abst. of Ger. Offen. 2,654,668, Pub. Dec. 3, 1975).
Ali et al., J. Chem. Soc. Perkin 1, 1976, pp. 1934–1938.
Roberts, J. Chem. Soc. Chem. Comm., 1974, pp. 948–949.
Corey et al., Tet. Lett. 4, pp. 311–313, (1970).
Huber et al., Helv. Chim. Acta., vol. 53, pp. 495–513, (1970).
Malinovskii, Epoxides and Their Derivatives, pp. 69–79, (1965).
J. F. W. McOmie, Protective Groups in Organic Chemistry, pp. 323–336, Plenum Press, London and NY (1973).
Chemical Abstracts, Eighth Collective Index, (vols. 66–75, 1967–1971), p. 1981S.

*Primary Examiner*—John D. Randolph
*Attorney, Agent, or Firm*—Bacon & Thomas

[57] ABSTRACT

The invention relates to (1α, 2α, 4α, 6α)-3-oxatricyclo[4.2.0.0$^{2,4}$]octane-7-one and derivatives thereof in which the ketone group is protected, which compounds are useful intermediates in the preparation of natural and synthetic prostaglandins. Processes for the preparation of these compounds are described and exemplified as are processes for their conversion into known prostaglandin intermediates.

9 Claims, No Drawings

NOVEL PROSTAGLANDIN INTERMEDIATES

This is a continuation of application Ser. No. 868,331, filed Jan. 10, 1978, now abandoned.

The invention relates to improvements in the synthesis of prostaglandin-type compounds. More particularly it relates to intermediates which may be of value in the stereospecific synthesis of naturally-occurring prostaglandins and their analogues.

The prostaglandins are a class of naturally occurring cyclopentane derivatives whose importance in medicine is rapidly increasing. They are biologically active in many physiological systems and they or substances which antagonise their effects have potential medicinal application in for example the control of fertility, blood pressure and inflammation, the predominant type of activity depending on the precise chemical structure. A more detailed summary of their various activities is given in British Patent Specification No. 1,396,206.

Considerable research has been carried out not only into the synthesis of natural prostaglandins but also into attempting to prepare analogues thereof having desirable agonist or antagonist activity. In view of the complex stereochemistry of the prostaglandin molecule, such synthesis as have been developed are complicated, involving a large number of steps, and means whereby the complexity of such synthesis may be reduced have considerable value. In particular, methods are required which, while applicable to the manufacture of natural prostaglandins, are also applicable to the preparation of analogues. We have now been able to prepare and isolate by a few simple reactions an intermediate which may subsequently be transformed stereospecifically into both natural prostaglandins and analogues thereof.

Thus, according to one feature of the present invention we provide the compound of formula I,

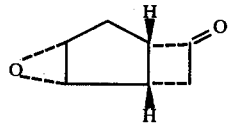

and derivatives thereof in which the ketone group is protected.

In the formulae I to IX inclusive set out herein, a broken line ---- connected to a ring substituent means that, with the ring substantially in the plane of the page, the substituent lies below the plane of the ring; a wedge ◂ means that the substituent to which it is attached lies above the plane of the ring. Such formulae as used herein are to be understood to depict both optical isomers of each of the compounds concerned as well as mixtures of said isomers, including racemates, even though the precise structure as set out relates only to one optical isomer.

The derivatives of the compound of formula I in which the ketone group is protected comprise compounds of general formula II,

wherein $Y^1$ and $Y^2$ together represent a protected keto group, e.g. a cyclic or acyclic ketal or thio ketal group. Preferably $Y^1$ and $Y^2$ together represent a group —A—$R^1$—A— where A represents an oxygen or sulphur atom and $R^1$ represents a $C_{2-6}$ alkylene group. Preferably the two groups A are bridged by a chain $R^1$ containing from 2 to 4 carbon atoms. Also preferred is that $Y^1$ and $Y^2$, which may be the same or different, each represent a group —A$R^2$ where A is as defined above and $R^2$ represents a $C_{1-6}$ alkyl group. Particularly preferred compounds are those wherein either $Y^1$ and $Y^2$ are the same and represent methoxy or butoxy groups or together they represent a 1,3-dioxolan, 1,3-dioxan or 1,3-dithian ring.

The compound of formula I and derivatives thereof in which the ketone group is protected may, for example, be prepared according to the following process which constitutes a further feature of the present invention, namely elimination of hydrogen halide from a compound of formula III,

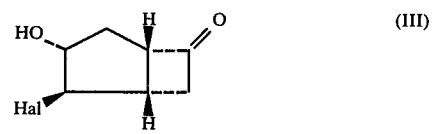

(wherein Hal represents a halogen atom e.g. a bromine, chlorine or iodine atom) or a derivative thereof in which the ketone group is protected.

Elimination may, for example, be effected in the presence of a base. Suitable bases include, for example, alkali metal alkoxides e.g. sodium methoxide or sodium butoxide. The elimination is preferably effected in the presence of a suitable solvent, for example an alcohol, e.g. methanol or t-butanol, or a hydrocarbon, e.g. benzene.

The compounds of general formula II may be prepared from compounds of formula III in which the ketone group is first protected by reaction with a reagent serving to introduce the ketone-protecting group.

Similarly for the preparation of compounds of general formula II, a compound of formula I as hereinbefore defined may be reacted with a reagent serving to introduce the ketone-protecting group.

Suitable methods for the introduction of ketone-protecting groups are well known. They include, for example, the formation of cyclic and acyclic ketals and thio ketals by reaction with an alcohol, thiol, dithiol or glycol. Protection with ethylene glycol is preferred. Such a reaction is preferably carried out in the presence of a solvent inert to the reaction conditions such as, for example, a hydrocarbon, e.g. benzene, or a halogenated hydrocarbon, e.g. dichloromethane or chloroform, and preferably in the presence of an acid catalyst, e.g. p-toluenesulphonic acid. It is preferred to use solvents such as benzene and dichloromethane which permit water formed in this reaction to be removed in the form of an azeotrope.

The compound of formula III wherein Hal represents a bromine atom is known from the literature [S. M. Roberts, J.C.S. Chem. Comm. 1974, 948]. The other compounds of general formula III wherein Hal is another halogen may be prepared by analogous processes or by halogen exchange reactions.

The compounds of general formula II may be used as intermediates in the stereospecific synthesis of prostaglandins. Thus, according to a still further feature of the present invention, we provide a process for the preparation of compounds of general formula IV,

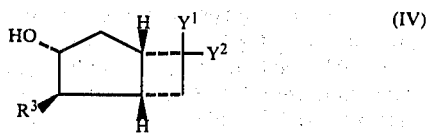

(wherein $Y^1$ and $Y^2$ are as hereinbefore defined and $R^3$ represents an optionally substituted $C_{1-12}$ aliphatic group) which comprises reacting a compound of formula II as hereinbefore defined with an organometallic reagent serving to introduce the group $R^3$.

The optionally substituted $C_{1-12}$ aliphatic group represented by $R^3$ may, for example, be an optionally substituted, straight or branched chain alkyl, alkenyl or alkynyl group. Substituents which may be present include, for example, phenyl, substituted phenyl (e.g. substituted by methyl, trifluoromethyl or halogen), $C_{3-7}$ cycloalkyl, $C_{5-7}$ cycloalkenyl, halogen (e.g. fluorine atoms), hydroxyl or protected or substituted hydroxyl.

The alkyl, alkenyl or alkynyl chain may, if desired, carry an oxo or protected oxo (e.g. ketal or cyclic ketal) group, or part of the chain may form part of a cycloalkyl or cycloalkenyl ring system.

The group $R^3$ is preferably a group of formula:

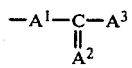

in which
$A^1$ represents trans $-CH=CB^1-$ (where $B^1$ represents a hydrogen atom or a methyl group); $-CH_2-CH_2-$; or $-C\equiv C-$;
$A^2$ represents an oxygen atom or a grouping of formula

(where $B^2$ represents a hydrogen atom or a methyl, ethyl, vinyl or ethynyl group and $B^3$ represents a hydrogen atom or a hydroxy protecting group) the carbon atom to which the groups $B^2$ and $OB^3$ are attached having the R or S configuration;
and $A^3$ represents a straight or branched chain $C_{1-9}$ alkyl radical optionally substituted with an oxo group, a hydroxy or protected hydroxy group or halogen atoms (e.g. fluorine); a straight or branched chain $C_{2-9}$ alkenyl radical; or a group $-B^4.B^5$ or $-B^4.O.B^5$ (where $B^4$ represents a $C_{1-5}$ alkylene group and $B^5$ represents a $C_{5-7}$ cycloalkyl or a phenyl group optionally substituted by one or more atoms or groups selected from halogen atoms [e.g. fluorine] and $C_{1-4}$ alkyl and $C_{1-4}$ haloalkyl [e.g. trifluoromethyl] groups).

Especially preferred groups for $R^3$ are groups of

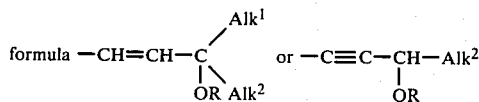

where R represents a hydroxy protecting group or a hydrogen atom, $Alk^1$ represents a hydrogen atom or a methyl, ethyl, vinyl or ethynyl group and $Alk^2$ represents a hydrogen atom or an alkyl group having up to 5 carbon atoms.

Substituted or protected hydroxyl groups present as substituents in $R^3$ may carry as the substituting or protecting group an aliphatic or cycloaliphatic group, which may contain an oxygen atom in the ring, an aromatic group (such as optionally substituted phenoxy, e.g. substituted with methyl, trifluoromethyl or halogen), a tri-(hydrocarbyl)silyl group or an acyl group. Such aliphatic and cycloaliphatic groups preferably have 1 to 8 carbon atoms. In general, a hydroxy protecting group may for example be an acyl, tri-(hydrocarbyl)silyl, alkoxymethyl, alkoxyethyl, trichloroethyl, tetrahydropyranyl or mono-, di- or tri-(monocyclicaryl)methyl group. When the protecting group is an acyl group then desirably this will be an alkanoyl, aralkanoyl or aroyl group, the alkanoyl group preferably containing not more than 7 carbon atoms, e.g. an acetyl group, and the aralkanoyl or arcyl groups preferably containing not more than 20 carbon atoms and being optionally substituted by one or more $C_{1-6}$ alkoxy groups, halogen atoms, nitro groups, $C_{1-10}$ acyloxy or $C_{2-7}$ alkoxycarbonyl groups.

When the protecting group is a tri(hydrocarbyl)silyl group, this will carry three hydrocarbon substituents, which may be the same or different, selected from $C_{1-6}$ alkyl, $C_{2-6}$ alkenyl, $C_{3-7}$ cyclalkyl, $C_{5-20}$ aralkyl, $C_{5-7}$ cycloalkenyl and $C_{6-20}$ aryl groups. Such groups will include, for example, methyl, ethyl, n-propyl, isopropyl, n-butyl, isobutyl, t-butyl, allyl, phenyl and benzyl groups. Preferred tri(hydrocarbyl)silyl groups are those in which the hydrocarbyl groups are methyl and/or t-butyl; the three alkyl groups need not all be the same. A particularly preferred protecting group is a t-butyldimethylsilyl group. When the protecting group is alkoxymethyl or alkoxyethyl, the alkoxy groups preferably contain from 1 to 6 carbon atoms and may themselves be substituted, e.g. by $C_{1-6}$ alkoxy groups. Thus, for example, the protecting group may be a 2-methoxyethoxymethyl, 1-methoxyethyl or 1-ethoxyethyl group.

In the case where the hydroxyl protecting group is a mono-, di- or tri-(monocyclicaryl)methyl group, this will desirably contain up to 20 carbon atoms and will preferably be a benzyl, diphenylmethyl or triphenylmethyl group.

Particularly useful hydroxyl protecting groups include tri(hydrocarbyl)silyl groups and 2-alkoxyethoxymethyl groups.

Particularly preferred groups $R^3$ are 3-(protected hydroxy)-oct-1-enyl groups e.g. a 3-t-butyldimethylsilyloxy-oct-1-enyl group.

The organometallic reagent, used in the reaction with the compound of formula II may, for example, be a copper-containing organometallic reagent.

The copper-containing organometallic reagent may, for example, be a compound of formula $Li[R^4 Cu R^{3a}]$ (wherein $R^{3a}$ is as hereinbefore defined for $R^3$ other than an ethynyl or 2-substituted ethynyl group and $R^4$ is the same as $R^{3a}$ or is the residue of a thiol or an ethynyl or 2-substituted ethynyl group). Alternatively the organometallic reagent may be a copper catalysed Grignard reagent $R^3$ Mg X (wherein $R^3$ is as hereinbefore defined including an ethynyl or 2-substituted ethynyl group and X represents a halogen atom e.g. chlorine, bromine or iodine) or an organo-copper reagent of formula Cu(R$^{3a}$)$_2$ (wherein R$^{3a}$ is as hereinbefore defined) in the presence of a metal salt Mg X$_2$ or Li X (where X is as defined above).

When the organometallic reagent is a compound of formula Li [R$^4$ Cu R$^{3a}$] the group R$^4$ preferably represents an arylthio group, e.g. phenylthio, or an ethynyl or 2-substituted ethynyl group, e.g. a 2-alkylethynyl group having 3-6 carbon atoms, for example a pent-1-ynyl group. This preference is a consequence of the nature of the reaction wherein only one of the carbon-containing side-chains in the copper-containing organometallic reagent is transferred to the compound of formula II. The remaining side chain is effectively wasted. It is therefore desirable, particularly when R$^{3a}$ is an expensive and lengthy side-chain, not to waste side-chain material and to employ as R$^4$ a group which bonds more strongly to the metal than R$^{3a}$. Arylthio, ethynyl and 2-substituted ethynyl groups are particularly suitable in this regard; for the same reason it is essential that the side-chain R$^{3a}$ does not contain a triple bond group in the α,β-position when such a copper-containing reagent is used.

Such a reagent will itself generally be prepared in solution prior to the reaction by methods well known in the art. For example, where R$^4$ is an arylthio, ethynyl or 2-substituted ethynyl group, the reagent may be prepared by admixture of the compound Cu R$^4$ with a lithium alkyl such as n-butyl lithium and the compound R$^{3a}$ X (where X is a halogen atom), in a hydrocarbon and/or ether solvent.

The reagent of formula Li [R$^4$ Cu R$^{3a}$] will also desirably contain additional solubilising groups thus having the formula Li [R$^4$ Cu R$^{3a}$(R$^5$)$_2$] where R$^5$ is a solubilising group. Such solubilising groups may take a variety of forms but phosphorus-containing organic groups are preferred. Particularly preferred groups are tris(dialkylamino)phosphine, trialkylphosphine and trialkylphosphite groups such as tris-(dimethylamino)-phosphine, tri-n-butylphosphine and trimethyl phosphite. These reagents having such solubilising groups will desirably be prepared in situ by methods known in the art e.g. by admixture of (i) a solution containing a hexalkyl-phosphorus triamide and the copper acetylide Cu R$^4$ with (ii) a lithium alkyl and a compound of formula R$^{3a}$ X.

Copper-catalysed Grignard reagents are a further useful source of carbon-containing side chains. Use of reagents of this type has the further advantage that C-terminal alkynyl groups may be added to the compound of formula Ia. The catalyst may, for example, be added in the form of either a cuprous or cupric salt e.g. a cuprous halide; such as cuprous iodide, bromide or chloride, or copper acetate.

Other suitable organometallic reagents include lithium aluminium complexes of the type Li Al (R$^6$)$_3$R$^{3b}$ where the groups R$^6$ represent alkyl groups which may be the same or different and R$^{3b}$ represents an alk-1-enyl group; an alane reagent (R$^6$)$_2$Al R$^{3c}$ where R$^6$ is as defined above and R$^{3c}$ represents an alk-1-ynyl or alk-1-enyl group; or a non-copper catalysed Grignard reagent R$^3$ Mg X wherein R$^3$ is as defined above including an ethynyl or 2-substituted ethynyl group and X is a halogen atom e.g. chlorine, bromine or iodine; a lithium acetylide of the type LiR$^{3d}$ where R$^{3d}$ is an ethynyl or 2-substituted ethynyl group; or a reagent of the formula Li$^+$[Alk$^3$S—CH=CH—CH$^-$—S Alk$^3$] and its various canonical forms where the groups Alk$^3$, which may be the same or different, are alkyl groups having 1-6 carbon atoms.

The last-mentioned reagent serves to introduce a grouping of the formula —CH(SAlk$^3$)—CH=CHS Alk$^3$. On cleavage with a heavy metal salt e.g. mercuric chloride and a base such as potassium carbonate this grouping yields a grouping —CH=CH—CHO which can be reacted according to known methods to yield, for example, a chain of the type commonly found in naturally occurring prostaglandins.

Reaction of the compound of formula II with an alane reagent (R$^6$)$_2$Al R$^{3c}$ has the advantage that the reaction temperature may be ambient temperature or above e.g. about 80° C. Reaction of the compound of formula II with copper-catalysed Grignard reagents will desirably be effected at or around 0° C., whereas reaction with reagents of formula Li[R$^4$Cu R$^{3a}$] will desirably be effected at much lower temperatures e.g. from −55° C. to −85° C., preferably around −78° C. Solvents which may be used for the reaction will be those conventionally used in organometallic chemistry and will be aprotic and preferably polar. Suitable solvents include ethers, (e.g. diethyl ether, tetrahydrofuran, dioxan or dimethoxyethane) and hydrocarbons (e.g. hexane or petroleum ether).

The regiospecific opening of the epoxide of formula II to yield mainly the desired compound of formula IV rather than the unwanted isomer could not have been predicted and represents a particularly valuable aspect of the present invention. The epoxide of formula II is thus a particularly valuable intermediate.

The compound of formula IV thus formed may, if desired, be subsequently deprotected to give a compound of formula V,

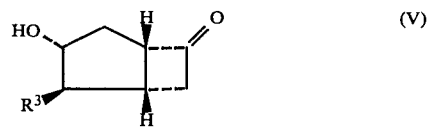

(wherein R$^3$ is as defined above).

Suitable methods for effecting deprotection are well known in the art. Thus, for example, cyclic and acyclic ketals may be conveniently cleaved to the ketone by acid, e.g. p-toluenesulphonic acid in the presence of a ketone, e.g. acetone; or organic acids such as trifluoroacetic acid or dilute aqueous mineral acids, preferably in the presence of an inert solvent such as, for example, tetrahydrofuran or acetonitrile. Thioketals may be cleaved, for example, by treatment with a heavy metal salt, e.g. mercuric chloride; the reaction will be effected in the presence of a suitable solvent, e.g. aqueous acetonitrile and preferably in the presence of an acid binding agent.

The compound of formula V may then itself desirably be reacted with a compound capable of protecting the hydroxyl group to give a compound of formula VI,

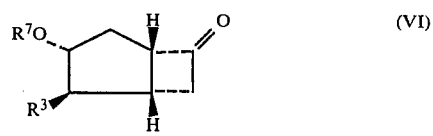

(wherein R$^3$ is as hereinbefore defined and R$^7$ represents a hydroxy protecting group). R$^7$ may, for example, be one of the hydroxyl protecting groups set out above in relation to $R^3$.

The conversion of the compound of formula V into the compound of formula VI may involve the acylation, silylation, trichloroethylation, alkoxyalkylation or aralkylation of the hydroxy group in the compound of formula V, suitable methods being well known in the art. Thus, for example, such protection may be effected with a compound of formula $R^7$-Z (wherein Z represents a readily eliminated substituent, for example, a halogen atom e.g. a chlorine atom). Such protection is preferably effected in a solvent such as dimethylformamide and preferably in the presence of an organic base, for example, imidazole.

Alternatively, the compound of formula V may be reacted with dihydropyran in the presence of an acid catalyst such as phosphorus oxychloride or p-toluenesulphonic acid, in an inert solvent e.g. a hydrocarbon such as benzene.

According to an alternative and preferred reaction route, the compound of formula IV may be reacted with a compound capable of protecting the hydroxyl group to give a compound of formula VII,

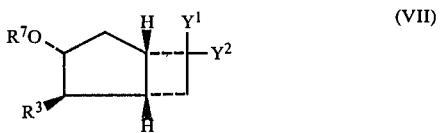
(VII)

(wherein $Y^1$, $Y^2$, $R^3$ and $R^7$ are as hereinbefore defined), and the compound of formula VII thus obtained may then, if desired, be deprotected to yield a compound of formula VI as hereinbefore defined. Suitable methods for the introduction of the group $R^7$ are those described above in relation to the conversion of a compound of formula V into a compound of formula VI. Suitable methods of deprotection are those described above in relation to the conversion of a compound of formula IV into a compound of formula V.

It will be appreciated that, when obtaining a compound of formula VI from a compound of formula IV, the order in which the removal of the ketone protecting group and the protection of the hydroxyl group with the group $R^7$ is carried out and the reaction conditions employed will depend on the relative reactivity of the ketone protecting group, the group $R^7$ and any reactive group in the grouping $R^3$. Thus, for example, when $Y^1$ and $Y^2$ together represent a 1,3-dioxolan group and $R^7$ represents a t-butyldimethylsilyl group it is preferred to carry out the removal of the 1,3-dioxolan group prior to protection of the hydroxyl group with the silyl group. It will be further appreciated that when the compounds of formula IV, VI or VII contain other protected ketone or hydroxyl groups then these are preferably less readily cleaved than groups which it is desired to remove.

According to a still further feature of the present invention there is provided a process for the preparation of compounds of general formula VIII,

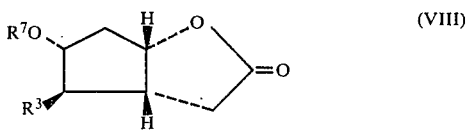
(VIII)

(wherein $R^3$ and $R^7$ are as hereinbefore defined) which comprises subjecting a compound of formula VI as hereinbefore defined to a Baeyer-Villiger-type oxidation. Where the group $R^7O$ is stable to the acid and alkaline conditions employed, it is preferred for the oxidation to be effected by means of alkaline hydrogen peroxide; in this case the initial product is a hydroxy acid salt which, on acidification, forms the desired lactone of formula VIII. The oxidation may also, for example, be effected by means of a peracid such as peracetic acid, trifluoroperacetic acid, performic acid, perbenzoic acid, a halogenated perbenzoic acid e.g. m-chloroperbenzoic acid or a persulphuric acid. Preferably oxidations using peracetic, trifluoroperactic or performic acid are carried out in the presence of the corresponding carboxylic acid as solvent and in the presence of an alkali metal salt of the carboxylic acid. Oxidations using perbenzoic or halogenated perbenzoic acids will desirably be effected in an inert solvent e.g. a halogenated hydrocarbon such as dichloromethane or chloroform and preferably at a temperature between ambient temperature and about 0° C. The presence of a mild inorganic base to neutralise any carboxylic acid formed is also desirable e.g. an alkali metal carbonate or bicarbonate.

It is clearly desirable that any groupings in the substituent $R^3$ which might be affected by the peroxo reagent, e.g. keto groups, are in protected form, e.g. as ketals.

The Baeyer-Villiger reaction may in general be carried out at a temperature in the range $-50°$ to $+100°$ C., preferably $-10°$ to $+20°$ C.

There is some tendency for acyl and silyl groups to be removed during peracid oxidation but, in general, this merely yields a proportion of a corresponding hydroxyl compound which may readily,. if desired, be reprotected.

Compounds of general formula VIII are generally known in the literature as intermediates in syntheses of prostaglandins.

Partial reduction of a lactone of formula VIII, e.g. using di-isobutyl aluminium hydride, yields a hemiacetal which in the aldehyde form may be reacted e.g. with Wittig reagents, to form natural or novel prostaglandins.

The compound of general formula V and derivatives thereof in which the hydroxyl and/or ketone group is protected are novel compounds and constitute a further feature of the invention. The compounds of formulae IV, V, VI and VII together constitute a group of compounds having the general formula IX,

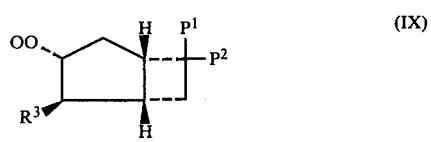
(IX)

wherein $R^3$ is as hereinbefore defined, Q represents a hydrogen atom or is as hereinbefore defined for $R^7$ and either $P^1$ and $P^2$ together represent a keto group or $P^1$ and $P^2$ are as hereinbefore defined for $Y^1$ and $Y^2$ respectively.

The following non-limiting Examples serve to illustrate the present invention. All temperatures are in °C.

EXAMPLE 1

(1α,2α,3β,5α)-3-Hydroxy-2-iodo-bicyclo[3,2,0]heptan-6-one

A solution of potassium iodate (8.56 g) in 2 N sulphuric acid (20 ml) and water (150 ml) was added to a solution of bicyclo[3,2,0]hept-2-en-6-one (21.6 g) in dioxan (100 ml) at 50°–60°, followed by portionwise addition of iodine (20.3 g). The resulting mixture was stirred for 4 hours at 50°–60°.

The reaction mixture was cooled to room temperature and extracted with ether (4×250 ml). The combined organic layers were washed with sodium thiosulphate solution (500 ml), dried over magnesium sulphate, and concentrated under reduced pressure to give a yellow oil. This material crystallised from ether/petroleum ether (b.p. 60°–80°) to give the title compound (26.0 g) as colourless crystals, m.p. 101°–102°.

$\nu_{max}$ (CHBr$_3$ solution) 3585 (O—H stretch), 1780 (C=O stretch), 1090, 1060, 985, 760 cm$^{-1}$.

$\tau$(CDCl$_3$ solution) 5.25 (1H, multiplet, C-3 proton), 5.70 (1H, singlet, C-2 proton), 6.0–7.0 (4H, complex), 7.0–7.9 (3H, complex).

EXAMPLE 2

1α,2α,3β,5α)-2-Chloro-3-hydroxybicyclo[3,2,0]heptan-6-one

A mixture of 1 N sodium hypochlorite in 0.1 N sodium hydroxide (478 ml) and 2 N sulphuric acid (425 ml) was added to a solution of bicyclo[3,2,0]hept-2-ene-6-one (23.0 g) in acetone (500 ml). The resulting solution was stirred at room temperature for 24 hours.

Acetone was removed under reduced pressure and the residue neutralised with 8% sodium bicarbonate solution (250 ml) and water (200 ml). The aqueous solution was extracted with ethyl acetate (3×500 ml). Removal of solvent after drying over magnesium sulphate gave a pale yellow oil, which crystallised from petroleum ether (b.p. 60°–80°)/ethyl acetate to give the title compound (12.95 g) as colourless crystals, m.p. 69°–71°.

$\nu_{max}$ (CHBr$_3$ solution) 3580 (free O—H stretch), 1775 (C=O stretch), 1065, 990, 912, 788 cm$^{-1}$.

$\tau$(CDCl$_3$ solution) 5.49 (1H, doublet, C-3 proton), 5.71 (1H, singlet, C-2 proton), 5.9–6.4 (1H, multiplet, C-5 proton), 6.5–7.0 (3H, complex), 7.2–8.0 (3H, complex).

EXAMPLE 3

(1α,2α,3β,5α)-2-Iodo-spiro(bicyclo[3.2.0]heptane-6,2'-[1,3]dioxan)-3-ol

A solution of the product of Example 1 (22.0 g) in propane-1,3-diol (66.3 g), trimethylorthoformate (2.14 g) and p-toluene sulphonic acid (830 mg) was left standing at room temperature for 24 hours.

The reaction mixture was poured into 8% sodium bicarbonate solution (250 ml) and extracted with ether (4×250 ml). The combined organic extracts were washed with water (200 ml) and dried over sodium sulphate.

Removal of solvent under reduced pressure gave the title compound (30.0 g).

An analytical sample was purified by bulb-to-bulb distillation.

$\nu_{max}$ (liquid film) 3440, (0—H stretch), 2960, 2860, 1290, 1255, 1100, 1022, 960, 845, 820 cm$^{-1}$.

$\tau$(CDCl$_3$) 5.4 (1H, doublet, C-3 proton), 5.7 (1H, singlet, C-2 proton), 5.9–6.3 (5H, multiplet, complex), 6.6–7.0 (2H, complex), 7–8.8 (6H, complex).

EXAMPLE 4

(1α,2α,3β,5α)-2-Chloro-6,6-dimethoxy-bicyclo[3.2.0]heptan-3-ol

A solution of the product of Example 2 (2.0 g) in trimethyl orthoformate (2.65 g), methanol (4.0 g) and p-toluenesulphonic acid (114 mg) was left standing at room temperature for 4 days.

The reaction mixture was poured into 8% aqueous sodium bicarbonate (25 ml) and water (20 ml) and extracted with dichloromethane (4×50 ml). The combined organic extracts were washed with water (25 ml) and dried over sodium sulphate.

Concentration under reduced pressure gave the title compound as a yellow oil (2.7 g). Spectroscopic data were obtained for an analytical sample purified by thin layer chromatography on silica gel (50% ethyl acetate-petroleum ether (b.p. 60°–80°) as eluant, Rf 0.4).

$\nu_{max}$ (CHBr$_3$ solution) 3430 (intramolecularly bonded O—H stretch), 1240, 1040, 915, 848, 825, 790, 760 cm$^{-1}$.

$\tau$(CCl$_4$ solution) 5.75 (1H, multiplet, C-3 proton), 5.97 (1H, multiplet C-2 proton), 6.45 (1H, broad singlet, —OH), 6.1–7.5 (8H, complex), 7.5–8.2 (4H, complex).

EXAMPLE 5

(1α,2α,3β,5α)-2-Bromo-spiro(bicyclo[3.2.0]heptane-6,2'-[1,3]dithiolan)-3-ol

A solution of (1α,2α,3β, 5α)-2-bromo-3-hydroxybicyclo[3.2.0]heptan-6-one (4.0 g) and ethane-1,2-dithiol (1.84 g) in benzene (50 ml) was treated with p-toluenesulphonic acid (200 mg) and boiled under reflux for 8 hours.

The reaction mixture was cooled, poured into 8% sodium bicarbonate solution (50 ml) and extracted with ethyl acetate (4×50 ml). Concentration under reduced pressure after drying over sodium sulphate gave the title compound (3.9 g) as an off-white crystalline solid m.p. 73°–75°.

$\nu_{max}$ (CHBr$_3$ solution) 3590 (O—H stretch), 1450, 1268, 1040, 1030, 945, 853, 775, 750 cm$^{-1}$.

$\tau$(CCl$_4$ solution) 5.5 (1H, multiplet, C-3 proton), 5.9 (1H, singlet, C-2 proton), 6.7–7.5 (9H, complex including OH), 6.85 (multiplet, —CH$_2$S—), 7.5–7.7 (2H, multiplet, C-4 proton).

EXAMPLE 6

(1α,2α,3β,5α)-2-Bromo-6,6-dimethoxybicyclo[3.2.0]heptan-3-ol (1α,2α,3β,5α)-2-Bromo-3-hydroxybicyclo[3.2.0]heptan-6-one (10.25 g), trimethyl orthoformate and 4-toluene sulphonic acid (0.19 g) were stirred in methanol (100 ml) for 72 hr. Methanol was removed under reduced pressure, the product dissolved in ether (100 ml), washed with 8% sodium bicarbonate solution (2×100 ml), water (100 ml), dried and evaporated to give a yellow viscous oil (11.7 g) a sample (0.61 g) of which was subjected to Kugelrohr distillation at 0.2 torr/130° to give the title compound as a colourless oil (0.485 g).

$\nu_{max}$ (CHBr$_3$ solution) 3420 (intramolecularly hydrogen bonded O—H), 1050 cm$^{-1}$.

$\tau$(CDCl$_3$ solution) 5.53 (1H, doublet, CH—O—), 5.80 (1H, broad singlet, CHBr), 6.2 (1H, broad singlet, OH), 6.83 (6H, singlet, 2×OCH$_3$).

EXAMPLE 7

(1α,2α,3β,5α)-2-Bromo-spiro(bicyclo[3.2.0]heptane-6,2'-[1,3]dioxolan)-3-ol (1α,2α,3β,5α)-2-Bromo-3-hydroxy-bicyclo[3.2.0]heptan-6-one (125.0 g), ethylene glycol (57.0 g) and p-toluenesulphonic acid (1.2 g) were heated at reflux in dry benzene (1200 ml) under nitrogen atmosphere for 18 hours. Water was removed using a Dean and Stark trap.

The yellow solution was then washed with 8% sodium bicarbonate solution (4×500 ml) and water (2×500 ml) and dried over sodium sulphate. Removal of benzene under reduced pressure gave the title compound (148 g).

$\nu_{max}$ (liquid film) 3460 (broad O—H stretch), 2950, 2890, 1420, 1320, 1300, 1180, 1120, 1022, 948, 915, 840, 820, 779, 700 cm$^{-1}$.

$\tau$(CDCl$_3$ solution) 5.5 (1H, broad triplet, C-3 proton), 5.75 (1H singlet, C-2), 5.9–6.1 (5H, complex, —OCH$_2$C-H$_2$O— and —OH), 6.5–7.75 (5H, complex), 7.95 (1H, broad doublet, C-4α proton).

EXAMPLE 8

(1'α,2'α,4'α,6'α)-spiro(1,3-Dioxane-2,7'-[3']oxatricyclo[4.2.0.0$^{2,4}$]octane)

A solution of sodium hydroxide (4.45 g) in methanol (80 ml) was added to a solution of the product of Example 3 (15.0 g) in methanol (30 ml) and the mixture stirred at room temperature for 40 hours.

The reaction mixture was poured into water (250 ml) and extracted with dichloromethane (4×50 ml). The combined extracts were washed with water (25 ml), dried over magnesium sulphate, and concentrated under reduced pressure to give an oil. The experiment was repeated and the combined products distilled bulb-to-bulb at 80°–90°/0.1–0.5 torr to give the title compound (9.0 g).

$\nu_{max}$(liquid film) 3010, 2960, 2860, 1320, 1290, 1260, 1150, 1105, 1073, 971, 850, 840 cm$^{-1}$.

$\tau$(CDCl$_3$ solution) 6.0–6.7 (6H, complex, 2×—CH$_2$—O— and CH—O—), 6.8–8.8 (8H, complex).

EXAMPLE 9

(1α,2α,4α,6α)-7,7-Dimethoxy-3-oxatricyclo[4.2.0.0$^{2,4}$]octane (a)

Sodium metal (2.76 g) was added to methanol (100 ml) and the mixture heated at reflux for ½ hr, then cooled to −5°. A solution of the product from Example 6 (10 g) in methanol (30 ml) was added slowly, the mixture allowed to warm to 20° and stirred for 24 hr. The solution was evaporated under reduced pressure to low volume (20 ml), diluted with water (250 ml) and extracted with ether (3×100 ml). The combined organic layers were washed with water (100 ml), dried and evaporated to give the title compound as a yellow oil (5.5 g).

Kugelrohr distillation at 0.01 torr/100° gave the title compound as a colourless oil (4.28 g).

$\nu_{max}$ (CHBr$_3$ solution) 2830, 1255, 1035, 850, 840 cm$^{-1}$. $\tau$(CDCl$_3$ solution) 6.32 (1H, triplet, CH—O), 6.48 (1H, triplet, CH—O), 6.83 (3H, singlet, OCH$_3$), 6.92 (3H, singlet, OCH$_3$).

(b)

(1α,2α,4α,6α)-7,7-Dimethoxy-3-oxatricyclo[4.2.0.0$^{2,4}$]octane

A solution of sodium hydroxide (0.89 g) in methanol (15 ml) was added to a solution of the product of Example 4 (2.0 g) in methanol (5 ml) and the mixture stirred at room temperature for 24 hours.

The reaction mixture was poured into water (200 ml) and extracted with dichloromethane (4×50 ml). The combined organic layers were washed once with water and dried over magnesium sulphate.

Concentration under reduced pressure gave the title compound as a colourless oil (1.7 g) identical to the product from Example 9(a).

EXAMPLE 10

(1'α,2'α,4'α,6'α)-spiro(1,3-Dioxolane-2,7'-[3']oxatricyclo[4.2.0.0$^{2,4}$]octane)

A solution of sodium methoxide [from sodium metal (40.5 g) and Analar methanol (1.2 liters)] was cooled to 0° and treated dropwise with a solution of the product of Example 7 (147.0 g) in methanol (2 liters). The reaction mixture was stirred at room temperature for 48 hours, poured into water (2 liters) and extracted with dichloromethane (5×500 ml).

The combined organic extracts were washed with water (250 ml) and dried over magnesium sulphate.

Removal of solvent gave the title compound as a pale yellow oil (85.0 g). Bulb-to-bulb distillation at 100°/0.15 torr gave an analytical sample.

$\nu_{max}$ (liquid film) 3000, 2950, 2885, 1320, 1288, 1188, 850 cm$^{-1}$.

$\tau$(CDCl$_3$ solution) 6.0–6.5 (6H, —OCH$_2$CH$_2$O— and —CH—O—CH—), 6.8 (1H, broad multiplet, C-6' α proton), 7.2–7.7 (3H, complex) 7.7 (1H, quartet, C-5'β proton), 8.2 (1H, octet, C-5'α proton).

EXAMPLE 11

(1α,2α,4α,6α)-7,7-Dibutoxy-3-oxatricyclo[4.2.0.0$^{2,4}$]octane

A solution of (1α,2α,3β,5α)-2-bromo-3-hydroxybicyclo[3.2.0]heptan-6-one (4.0 g), n-butanol, (14.45 g) and p-toluenesulphonic acid (200 mg) was boiled under reflux in dry benzene (60 ml) for 24 hours using a Dean and Stark trap.

The reaction mixture was then cooled, treated with tetrabutyl ammonium hydroxide (25.29 g, 40% solution in water) and stirred for 23 hours at 20°. The benzene layer was separated and the aqueous layer extracted with dichloromethane (4×50 ml). The combined organic layers were washed with water (50 ml) and brine (50 ml).

The residual oil, obtained after removal of solvent under reduced pressure, was filtered through a column of silica gel (100 g) by eluting with ether (1 liter). Solvent was removed from the filtrate and the resulting brown oil distilled, using bulb-to-bulb distillation apparatus at 130°/0.75 torr, to give the title compound (4.3 g).

An analytical sample was obtained by thin layer chromatography on silica gel (50% ethyl acetate petroleum ether (b.p. 60°–80°) as eluant, Rf 0.5).

$\nu_{max}$ (liquid film) 3020, 2965, 2940, 2880, 1315, 1252, 1203, 1180, 1140, 1070, 845 cm$^{-1}$.

$\tau$(CCl$_4$ solution) 6.5 (1H, triplet, C-2 proton), 6.7 (1H, triplet, C-4 proton), 8.9–9.3 (6H, multiplet, 2×RCH$_2$CH$_3$).

EXAMPLE 12

(1α,2α(E),3β,5α)-2-[3-[[(1,1-dimethylethyl)dimethylsilyl]oxy]-1-octenyl]-spiro[bicyclo[3.2.0]heptane-6,2'-[1,3]dioxolan]-3-ol A solution of n-butyl lithium (17.3 ml of 1.9 M hexane solution) was added dropwise at −70°, under a nitrogen atmosphere, to a stirred solution of 1-iodo-3-[[(1,1-dimethylethyl)-dimethylsilyl]oxy]-oct-1-ene (12.05 g). After stirring for 1 hr at −70° a solution of copper pentyne (4.3 g) in dry ether (20 ml) containing hexamethylphosphorus triamide (12 ml) was added dropwise thereto. The resulting yellow solution was stirred for 1 hr. and then a solution of the product of Example 10 (5.0 g) in ether (10 ml) was added dropwise thereto. A pale yellow precipitate formed almost immediately. The reaction mixture was allowed to warm to −30° and was stirred at this temperature for 18 hr. After quenching with saturated ammonium chloride solution (50 ml) the organic layer was removed and stirred with ice-cold 2 N sulphuric acid (50 ml). The salts thus precipitated were filtered off and the organic layer was separated. This extract was washed with water (2×50 ml) and dried (Na$_2$SO$_4$). Evaporation of the solvent under reduced pressure afforded a pale yellow oil (13.2 g) which was chromatographed on silica gel (500 g) collecting 100 ml fractions.

Elution with ethyl acetate/petroleum ether (b.p. 60°–80°) (1:9) afforded in fractions 5–10 excess octene (3.0 g). Further elution with ethyl acetate/petroleum ether (b.p. 60°–80°) (3:7) and evaporation of the solvent gave the title compound as a pale yellow oil (5.5 g) in fractions 38–85.

TLC Single spot Rf 0.74 [(silica gel)-ethyl acetate/petroleum ether (b.p. 60°–80°) (1:1)-2,4-dinitrophenylhydrazine]CHBr$_3$.

$\nu$max (CHBr$_3$ solution) 3580 (—OH), 1250 (Si—Me), 1060 (Si—O), 970 (trans C=C) cm$^{-1}$.

EXAMPLE 13

[1α,2α(E),3β,5α]-2-[3-Methyl-3-[(trimethylsilyl)oxy]-1-octenyl]-spiro[bicyclo[3,2,0]heptane-6,2'-[1,3]dioxan]-3-ol A solution of (E)-1-iodo-3-methyl-3-[(trimethylsilyl)oxy]-1-octene (5.10 g) in dry ether (50 ml) was cooled to −70° under nitrogen and treated with a 1.5 M solution of n-butyl lithium in hexane (10 ml). After 30 min at −70° the colourless solution was treated with cuprous thiophenoxide (2.59 g). The resulting yellow suspension was stirred at −70° for 20 min, −30° for 30 min, and was then treated at −40° with a solution of the product of Example 8 (1.82 g) in dry ether (20 ml). After 2 hr at −30° to −40°, the reaction mixture was shaken with saturated aqueous ammonium chloride (100 ml) and filtered to remove the cuprous thiophenoxide. The filtrate was extracted with ethyl acetate (3×50 ml). The combined organic extracts were dried over sodium sulphate and concentrated under reduced pressure to give an oil (6.06 g; ratio of regioisomers 63:37). Chromatography on silica gel eluting with 50% ethyl acetate in light petroleum (b.p. 60°–80°) afforded pure title compound (0.58 g) as a colourless oil.

$\nu_{max}$ (CCl$_4$ solution) 3600 (free O—H stretch, weak band), 3490 (intramolecularly bonded O—H stretch, strong band); $\nu_{max}$ (CHBr$_3$ solution) 1250 and 840 (Si—CH$_3$ bands) cm$^{-1}$.

$\tau$(C$_6$D$_6$) 4.30–4.80 (2H, AB part of ABX system, olefinic protons), 5.90 (1H, multiplet, —CHO—), 6.43–6.80 (4H, multiplet, —CH$_2$O—), 6.82–7.17 (2H, multiplet), 7.30 (1H, multiplet), 7.43–8.23 (5H, complex), 8.30–8.90 (13H, complex including singlet at 8.72 for tertiary CH$_3$), 9.10 (3H, triplet, terminal CH$_3$), 9.80 (9H, singlet, Si—CH$_3$).

EXAMPLE 14

(1α,2α,3β,5α)-2-Butyl-6,6-dimethoxybicyclo[3.2.0]heptan-3-ol n-Butyllithium in hexane (1.6 M (61.8 ml)) was added to copper (I) iodide (9.38 g) in dry ether (100 ml) at −70°. The mixture was warmed to −30° and stirred for ¼ hr then cooled to −55° and the product of Example 9 (2.8 g) in ether (10 ml) added dropwise. After 2 hr, saturated ammonium chloride solution (100 ml) was added, the mixture allowed to stand for 16 hr, and the layers separated. The organic layer was dried, filtered through Hyflo, and evaporated to give the title compound as a yellow oil (3.05 g). (Ratio of regioisomers 70:30).

Short column chromatography on silica gel with 20% ethyl acetate in petrol as eluant gave a pure sample of the title compound (1.45 g).

$\nu_{max}$ (CHBr$_3$ solution) 3590 (free O—H weak), 3450 (intramolecularly hydrogen bonded O—H strong), 1040, 840 cm$^{-1}$.

$\tau$(CCl$_4$ solution) 6.20 (1H, multiplet, CH—O), 6.89 (3H, singlet, OCH$_3$), 6.93 (3H, singlet, OCH$_3$), 8.5–9.3 (9H, complex, —CH$_2$CH$_2$CH$_2$CH$_3$).

EXAMPLE 15

(1α,2α,3β,5α)-2-Butyl-spiro[bicyclo[3.2.0]heptane-6,2'-[1,3]dioxolan]-3-ol

A 2 M solution of butyl magnesium chloride in ether (34 ml) was cooled to −30° under nitrogen with stirring. The resulting slurry was treated with purified cuprous iodide (0.84 g) (G. B. Kauffman et al., Inorg. Synth., 1963, 7, 9) and stirred for 45 min at −30° to give a dark purple suspension. A solution of the product of Example 10 (8.40 g) in dry ether (35 ml) was then added dropwise over 25 min while the reaction mixture temperature was maintained at −30°. After addition was complete, the reaction mixture was stirred under nitrogen at −30° for 1 hr, and at −30° warming to 0° for the following 17 hr. Finally, the reaction mixture was shaken with saturated aqueous ammonium chloride (300 ml) and extracted with ether (3×100 ml). The combined ether extracts were dried over sodium sulphate and concentrated under reduced pressure to give the title compound as an oil (11.20 g; ratio of regioisomers 80:20).

An analytical sample obtained by preparative TLC (SiO$_2$, 5% methanol in dichloromethane, Rf 0.44) had $\nu_{max}$ (CCl$_4$) 3620 (free O—H stretch, weak band), 3525 (intramolecularly bonded O—H stretch, strong band) cm$^{-1}$.

$\tau$(C$_6$D$_6$) 6.04 (1H, broadened quartet, —CH—O—), 6.3–6.8 (4H, multiplet, —CH$_2$O—), 6.9 (1H, broad singlet, OH, ex D$_2$O), 7.0–7.7 and 7.8–8.45 (total 7H, complex), 8.5–9.0 (6H, complex, —CH$_2$CH$_2$CH$_2$—), 9.12 (3H, triplet, CH$_3$).

EXAMPLE 16

(1α,2α,3β,5α)-2-Ethenyl-spiro[bicyclo[3.2.0]heptane-6,2'-[1,3]-dioxolan]-3-ol

A 1.4 M solution of t-butyllithium in pentane (143 ml) was added over 30 min. to a stirred solution of vinyl bromide (10.7 g) in tetrahydrofuran (40 ml), ether (10 ml) and light petroleum (40°-60°)/(10 ml) at −120°. After stirring for one hour at −120° the mixture was warmed to −78° and a solution of 1-pentynyl copper (I) (13.05 g) in hexamethylphosphorus triamide (37.2 ml) and ether (100 ml) was added over 10 mins. The mixture was stirred for 1 hr at −78° and the product of Example 10 (8.4 g) in ether (20 ml) added over 5 min. The mixture was stirred for 2.5 hr at −70°, then allowed to stand for 64 hr at −15°.

Saturated ammonium chloride solution (400 ml) was added and the layers separated. The aqueous layer was washed with ether (300 ml) and the combined organic layers shaken with 2% sulphuric acid (500 ml) at 0°. The mixture was filtered through Hyflo, and the layers separated. The organic layer was washed with 8% sodium bicarbonate solution (400 ml), water (400 ml), dried and evaporated to give the title compound as a pale yellow oil (3.9 g). (Ratio of regioisomers (82:18).

Kugelrohr distillation of a sample at 0.1 torr/150° gave the title compound as a colourless oil.

$\nu_{max}$ (CHBr$_3$ solution) 3580 (free O—H), 3480 (intramolecularly hydrogen bonded O—H), 1635 (C=C).

$\tau$(CCl$_4$ solution) 4.4 (1H, multiplet, C$\underline{H}$=CH$_2$), 4.5-5.3 (2H, complex, CH=C$\underline{H}_2$), 6.0-6.3 (5H, complex, —CH—O— and O.CH$_2$.CH$_2$.O).

EXAMPLE 17

(1α,2α(E),3β,5α)-2-[3-[[(1,1-Dimethylethyl)dimethylsilyl]oxy]-1-undecenyl]-spiro[bicyclo[3.2.0]heptan-6,2'-[1,3]-dioxolan]-3-ol A 1.6 M solution of n-butyllithium in hexane (9.4 ml) was added to 1-iodo-3-[[(1,1-dimethylethyl)dimethylsilyl]oxy]-undecene (5.64 g) in dry ether (15 ml) at −78° under nitrogen. After 1 hr a solution of 1-pentynyl copper (I) (1.79 g) in hexamethylphosphorus triamide (5.11 ml) and dry ether (20 ml) was added dropwise, and the mixture stirred for a further 1 hr at −78°.

A solution of the product of Example 10 (2.09 g) in dry ether (20 ml) was added over 5 min, and the mixture stirred for 1 hr at −78°, then 16 hr at −30°. Saturated ammonium chloride solution (100 ml) was added, the organic layer separated and shaken with ice-cold 2% sulphuric acid (200 ml). The mixture was filtered through Hyflo, separated, and the organic layer washed with 8% sodium bicarbonate solution (200 ml), dried, and evaporated to give the crude product as a yellow oil (5.71 g) (ratio of regioisomers 80:20).

Short column chromatography on silica gel with 10% ethyl acetate in petroleum ether (b.p. 60°-80°) as eluant gave the title compound (3.35 g) as a colourless oil.

$\nu_{max}$ (CHBr$_3$ solution) 3600 (free OH-weak), 3480 (intramolecularly bonded OH) 1250, 839 (SiMe), 974 (trans CH=CH).

$\tau$(CDCl$_3$ solution) 4.7 (2H, multiplet, CH=CH), 5.93-6.3 (6H, multiplet, O.CH$_2$.CH$_2$.O and 2×CH—O—), 6.72-8.2 (8H, complex), 10.0 (6H, singlet, Si(CH$_3$)$_2$).

EXAMPLE 18

(1α,2α(E),3β,5α)-(3-Hydroxy-1-octynyl)-spiro[bicyclo[3.2.0]heptane-6,2'-[1,3]dioxolan]-3-ol A solution of n-butyl lithium (31.25 ml of a 1.6 M hexane solution) was added dropwise to a stirred solution of 3-[(trimethylsilyl)oxy]-1-octyne (9.9 g) (prepared according to J. Fried, C. H. Lin, J. C. Sih, P. Dalven and G. F. Cooper, J. Amer. Chem. Soc., 94, 4342 (1972)) in toluene (30 ml) at 0° under a nitrogen atmosphere. After 15 min. at 0° dimethylchloroalane (14.8 ml of a 25% solution) was added dropwise followed, after stirring for a further 1 hr, by a solution of the product of Example 10 (3.36 g) in toluene (10 ml). The mixture was heated at 80° with stirring for 8 hr, then cooled to 0° and quenched by addition of saturated aqueous sodium sulphate (100 ml). The mixture was clarified by filtration and the layers separated. The organic layer was washed with water (50 ml), dried (MgSO$_4$) and evaporated under reduced pressure to give an oil (15.15 g). This was dissolved in methanol (135 ml) and a solution of potassium carbonate (7.5 g) in water (30 ml) added. After stirring at 20° for 3 hr the methanol was removed by evaporation under reduced pressure and the residue extracted with ether (3×100 ml). The dried (MgSO$_4$) ethereal solution was evaporated and the residue (9.5 g) subjected to short column chromatography on silica gel (250 g) eluting with 3% ethanol-chloroform and collecting 15 ml fractions. Evaporation of fractions 31-90 gave the title compound as a pale yellow oil (3.7 g).

$\nu_{max}$ (CHBr$_3$ solution) 3590 (free O—H), 3470 (intramolecularly bonded O—H), (liquid film) 2230 (C≡C) cm$^{-1}$.

$\tau$(CDCl$_3$ solution) 5.5-5.85 (2H, complex, 2×C$\underline{H}$—O), 6.1 (4H, singlet, O.CH$_2$CH$_2$.O), 6.9 (1H, multiplet, bridgehead proton at C-5), 7.18 (1H, broad singlet, propargylic proton at C-2), 9.10 (3H, multiplet, CH$_2$C$\underline{H}_3$).

EXAMPLE 19

(1α,2α,3β,5α)-2-[1,3-Bis(methylthio)-2-propenyl]-spiro[bicyclo[3.2.0]heptane-6,2'-[1,3]dioxolan]-3-ol A 1.55 M solution of n-butyl lithium in hexane (84.5 ml) was added to a stirred solution of 1,3-bis(methylthio)-2-methoxypropane (E. J. Corey et al., J. Amer. Chem. Soc., 1971, 93, 1724; 10.9 g) and diisopropylamine (18.6 ml) in dry tetrahydrofuran (200 ml) at −70° C. under nitrogen. After being stored at 0°-5° C. for 2 hr, the deep purple solution was cooled to −70° C., treated with the product of Example 10 (10.0 g) over 20 min, and maintained at −70° for 2 hr. The reaction mixture was then allowed to warm slowly to −5° over 15 hr, and finally shaken with saturated aqueous ammonium chloride (250 ml). The aqueous layer was separated and extracted with ether (2×100 ml). The combined organic layers were then dried over magnesium sulphate and concentrated under reduced pressure to give an orange oil (19.0 g). Chromatography on silica gel with 25% ethyl acetate in petroleum ether (b.p. 60°-80°) removed non-polar impurities. Further elution with 50% ethyl acetate in petroleum ether (b.p. 60°-80°) gave the title compound (13.0 g, ratio of regioisomers 83:17) as a viscous, orange oil.

$\nu$(CCl$_4$) 3620 (free O—H stretch, weak band), 3520 (intramolecularly bonded O—H stretch, strong band), $\nu$(CHBr$_3$) 1598 (C=C stretch) cm$^{-1}$. $\tau$(CDCl$_3$)

3.65–4.15 (1H, complex, —C=CH—S—), 4.25–5.30 (1H, complex, —C=CH—C—), 5.60–6.35 (5H, broad multiplet overlapped by broad singlet, —CHO— and —CH₂O), 5.35–8.40 (15H complex).

EXAMPLE 20

[1α,2α(E),3β,5α]-[3-Hydroxy-spiro[bicyclo[3,2,0]heptane-6,2′-[1,3]dioxolan-2-yl]-2-propenal A solution of the product of Example 19 (605 mg, ratio of regioisomers 83:17) in 4:1 acetonitrile-water (30 ml) was treated with powdered calcium carbonate (1.2 g) followed by mercuric chloride (2.16 g). The resulting mixture was stirred under nitrogen for 3 hr at 50°, cooled and filtered through Hyflo. The filtrate was diluted with brine (50 ml) and extracted with ether (3×50 ml). The combined ether extracts were dried over sodium sulphate and concentrated under reduced pressure to give a brown oil (450 mg). Purification by preparative TLC (SiO₂, 2 elutions with 5% methanol in dichloromethane, Rf 0.28 [after 1 elution]) gave the title compound (126 mg) as a pale straw coloured viscous oil.

$\nu$(CHBr₃) 3590 (free O—H stretch, weak band), 3470 (intamolecularly bonded O—H, strong band, 2735 (aldehyde C—H stretch), 1680 (C=O stretch), 1632 (C=C stretch)cm⁻¹.

$\tau$(CDCl₃) 0.53 (1H, doublet, J=ca. 7.5 Hz, —CH=O), 3.35 (1H, double doublet, J=7.5 Hz and 16 Hz, —CH=C—C=O), 3.98 (1H, double doublet, J=7.5 Hz and 16 Hz, —C=CH—C=O), 5.87 (1H, quartet, —CHO—), 6.08 (4H, singlet, —CH₂O—), 6.45 (1H, broad singlet, OH, ex D₂O), 6.77–8.07 (7H, complex).

EXAMPLE 21

(1α,2α(E),3β,5α)-3-Hydroxy-2-(3-[1,1-dimethylethyl]-dimethylsilyloxy-1-octenyl)bicyclo[3,2,0]heptan-6-one A solution of p-toluenesulfonic acid (0.5 g) and the product of Example 12 (1.0 g) in acetone (20 ml) was allowed to stand at ~3° for 36 hr. Solid sodium bicarbonate was then added thereto and the resultant mixture was diluted with ether (20 ml). The solid was filtered off and the solvent evaporated under reduced pressure to afford title compound as a pale yellow liquid (0.6 g).

TLC shows a major component RF 0.48 [silica gel-methanol/benzene (1:4)-2,4-dinitrophenylhydrazine]

$\nu_{max}$ (CHBr₃ solution) 1772 (C=O) cm⁻¹.

EXAMPLE 22

(1α,2α(E),3β,5α)-3-Hydroxy-2-(3-hydroxy-1-octenyl)-bicyclo [3,2,0]heptan-6 one

A solution of the product of Example 12 (2.05 g) in acetonitrile (30 ml), water (10.5 ml) and 2 N sulphuric acid (4.5 ml) was stirred at 20° for 16 hr. 8% Aqueous sodium bicarbonate (75 ml) was added and the mixture extracted with ethyl acetate (3×50 ml). The dried (MgSO₄) extracts were evaporated to give a colourless oil (1.6 g). A sample (0.8 g) of this oil was purified by short column chromatography on silica gel (20 g) eluting with ethyl acetate and collecting 15 ml fractions. Evaporation of fractions 4–7 gave the title compound as a colourless oil (609 mg).

$\nu_{max}$ (CHBr₃ solution) 3600 (O—H), 1770 (C=O), 975 (trans CH=CH) cm⁻¹.

$\tau$(CDCl₃ solution) 4.3–4.7 (2H, complex, CH=CH), 5.7–6.1 (2H, complex, 2×CH-O), 6.40 (1H, multiplet, allylic proton at ring C-2), 9.10 (3H, multiplet, CH₂CH₃).

EXAMPLE 23

(1α,2α(E),3β,5α)-2-[3-[[(1,1-Dimethylethyl)dimethyl-silyl]oxy]-1-octenyl]-spiro[bicyclo[3,2,0]heptane-6,2′-[1,3]dioxolan]-3-ol, acetate ester Acetic anhydride (3.0 ml) was added to a solution of the product of Example 12 (1.0 g) in pyridine (3.0 ml). The solution was kept at 0° for 3 days then diluted with ether (35 ml) and washed with 8% aqueous sodium bicarbonate (2×10 ml) and saturated copper (II) sulphate solution (2×10 ml). The dried (MgSO₄) organic solution was evaporated to give the title compound (1.03 g) as a pale yellow oil.

$\nu_{max}$ (CHBr₃ solution) 1720 (C=O), 978 (trans CH=CH), 1250, 835 (Si—CH₃) 1070, 775 cm⁻¹.

$\tau$(CDCl₃ solution) 4.5 (2H, multiplet, CH=CH), 5.07 (1H, quartet, CH-OAc), 6.0 (1H, multiplet, CH—OSi), 6.1 (4H, broad singlet, O.CH₂.CH₂.O), 7.93 (3H, singlet, O.CO.CH₃), 9.98 (6H, singlet, Si(CH₃)₂).

EXAMPLE 24

(1α,2α(E),3β,5α)-3-Methoxy-2-[3[[(1,1-dimethylethyl)-dimethylsilyl]oxy]-1-octenyl]spiro[bicyclo[3,2,0]heptane-6,2′-[1,3]-dioxolane]

Sodium hydride (120 ml of an 80% dispersion in oil) was added to a solution of the product of Example 12 (820 mg) in anhydrous dimethylformamide (7.5 ml). Iodomethane (1.42 g) was added and the mixture stirred at 20° for 16 hr. The solution was diluted with water (25 ml) and extracted with petroleum ether (b.p. 60°-80°) (3×25 ml). The combined extracts were washed with water, dried (MgSO₄) and evaporated to give the title compound as a colourless oil (800 mg).

$\nu_{max}$ (CHBr₃ solution) 1252 and 836 (Si—CH₃), 1070 and 776 (Si—O), 970 (trans CH=CH) cm⁻¹.

$\tau$(CDCl₃ solution) 4.55 (2H, multiplet, CH=CH), 6.13 (4H, broad singlet, O.CH₂.O), 6.0, 6.3 (2H, complex, 2×CH—O), 6.67 (3H, singlet, OCH₃), 10.0 (6H, singlet, Si(CH₃)₂).

EXAMPLE 25

(1α,2α(E),3β,5α)-3-(Acetyloxy)-2-(3-hydroxy-1-octenyl)bicyclo[3,2,0]heptan-6-one A solution of the product of Example 23 (800 mg) in acetone (5.0 ml), acetic acid (5.0 ml) and water (2.0 ml) was heated at 50° for 20 hr. The solution was poured into 2 N aqueous sodium carbonate (50 ml) and extracted with petroleum ether (b.p. 60°-80°) (3×30 ml). The dried extracts were evaporated to give an oil (800 mg). This was subjected to short column chromatography on silica gel (50 g) eluting with ethyl acetate-petroleum ether (b.p. 60°-80°) (2:5) and 10 ml fractions were collected. Evaporation of fractions 75-100 afforded the title compund as a colourless oil (146.5 mg).

$\nu_{max}$ (CHBr₃ solution) 3590 (O—H), 1775 (C=O, cyclobutanone), 1730 (C=O, acetate), 970 (CH=CH) cm⁻¹.

$\tau$(CDCl₃ solution) 4.2–4.7 (2H, complex, CH=CH), 4.90 (1H, broad singlet, CHOAc), 8.00 (3H, singlet, O.CO.CH₃), 9.11 (3H, multiplet, CH₂CH₃).

EXAMPLE 26

(1α,2α(E),3β,5α)-3-Methoxy-2-[3-[[(1,1-dimethylethyl)dimethylsilyl]oxy]-1-octenyl[bicyclo[3,2,0]heptan-6-one A solution of the product of Example 24 (660 mg) and trifluoroacetic acid (1.0 ml) in acetone (9.0 ml) was stood at 20° for 1 hr. Potassium carbonate (2.5 g) was added, followed by water (50 ml) and the mixture extracted with chloroform (3×25 ml). The combined organic extracts were washed with water, dried (MgSO$_4$) and evaporated under reduced pressure. The residue was dissolved by dry dimethylformamide (50 ml) and imidazole (0.21 g) and t-butyldimethylchlorosilane (0.33 g) added. The solution was stood at 20° for 20 hr, then water (50 ml) added and the mixture extracted with chloroform (3×50 ml). The extracts were washed with water (10 ml), dried (MgSO$_4$) and evaporated under reduced pressure. The residue was purified by short column chromatography on silica gel (25 g) eluting with petroleum ether (b.p. 60°–80°)-ethyl acetate (10:1). 10 ml Fractions were collected and evaporation of fractions 9–12 gave the title compound as a colourless oil (297 mg).

$\nu_{max}$ (CHBr$_3$ solution) 1770 (C=O), 965 (trans CH=CH), 1250, 835 (Si—CH$_3$) 840, 775 cm$^{-1}$.

$\tau$(CDCl$_3$ solution) 4.3–4.8 (2H, complex, CH=CH), 5.97 (1H, multiplet, CH-OSi), 6.30 (1H, broadened doublet, CH-OMe), 6.40 (1H, multiplet, C-5 bridgehead proton), 6.75 (3H, singlet, OCH$_3$), 6.90 (1H doublet of doublets, allylic proton on ring C-2), 9.92 and 9.94 (6H, singlets, OSi(CH$_3$)$_2$).

EXAMPLE 27

(1α,2α(E),3β,5α)-3-[[(1,1-Dimethylethyl)dimethylsilyl]oxy]-2-[3-[(1,1-Dimethylethyl)dimethylsilyl]oxy-1-octenyl]bicyclo[3,2,0]heptan-6-one To a stirred solution of the product of Example 21 (0.8 g) in dry dimethylformamide (10 ml) was added imidazole (0.42 g) and (1,1-dimethylethyl)-dimethylsilyl chloride (0.66 g). The mixture thus obtained was stirred for 1 hr before being allowed to stand overnight. After quenching with water (40 ml) the mixture was extracted with petroleum ether (b.p. 60°–80°) (3×20 ml). The combined extracts were washed with water (30 ml) and dried (Na$_2$SO$_4$). Evaporation of the solvent under reduced pressure afforded a yellow liquid (1.0 g) which was chromatographed on silica gel (50 g). Elution with ethyl acetate/petroleum ether (b.p. 60°–80°) (1:9) and evaporation of solvent gave the title compound as a colourless oil (0.8 g). b.p. ~180°/0.01 mm Hg.

EXAMPLE 28

(1α,2α(E),3β,5α)-3-[(Tetrahydro-2H-pyran-2-yl)oxy]-2-[3-[(tetrahydro-2H-pyran-2-yl)oxy]-1-octenyl]bicyclo[3.2.0]heptan-6-one Dihydropyran (1.0 ml) was added to a stirred solution of the product of Example 22 (0.8 g) and p-toluenesulphonic acid monohydrate (50 mg) in dry dioxan (7.0 ml). After 3 hr at 20° the solution was diluted with ether (50 ml), washed with 2 N sodium carbonate solution (15 ml), dried (MgSO$_4$) and evaporated. The residue was purified by short column chromatography on silica gel (25 g) eluting with 10% ethyl acetate-petroleum ether (b.p. 60°–80°) and collecting 15 ml fractions. Evaporation of fractions 9–24 gave the title compound as a colourless oil (908 mg).

$\nu_{max}$ (CHBr$_3$ solution) 1775 cm$^{-1}$ (C=O).

$\tau$(CDCl$_3$ solution) 4.3–4.9 (2H, complex, CH=CH), 5.23 and 5.4 (2H, broad singlets, —O—CH—O), 9.12 (3H, multiplet, CH$_2$CH$_3$).

EXAMPLE 29

(1α,2α(E),2β,5α)-3-[(Trimethylsilyl)oxy]-2-[3-[(trimethylsilyl)oxy]-1-octenyl]bicyclo[3,2,0]heptan-6-one A mixture of the product of Example 22 and bis(trimethylsilyl)trifluoroacetamide (0.05 ml) was stood at 20° until homogenous (4 hr). Excess silylating agent was evaporated under reduced pressure to give the title compond (492 mg) as a yellow oil.

$\nu_{max}$ (liquid film) 1780 (C=O) cm$^{-1}$.

$\tau$(CDCl$_3$ solution) 4.4–4.8 (2H, multiplet, CH=CH), 5.7–6.2 (2H, complex, 2×—CH—O—), 6.4 (1H, multiplet, C-2 proton), 9.12 (3H, multiplet (CH$_2$-CH$_3$), ca. 9.9 (18H, singlets, 2×Si(CH$_3$)$_3$).

EXAMPLE 30

(3aα,4α,5β,6aα)-5-[[(1,1-Dimethylethyl)dimethylsilyl]oxy]-4-[3-[[(1,1-dimethylethyl)dimethylsilyl]oxy]-1-octenyl]hexahydro-2H-cyclopenta[b]furan-2-one A 28% solution of hydrogen peroxide (1.1 ml) and 0.5 M sodium hydroxide solution (9.2 ml) were added at 3° under a nitrogen atmosphere to a stirred solution of the product of Example 27 (2.2 g) in methanol (100 ml). After stirring for 3 hr the resultant mixture was left to stand at ~5° for 72 hr. The solution was then diluted with brine (250 ml) and acidified to pH4 with 2 N hydrochloric acid before extracting with ether (4×50 ml). The combined ether extracts were washed with 8% sodium bicarbonate (50 ml), 10% sodium sulphite (50 ml) and water (2×50 ml) and dried (Na$_2$SO$_4$). Evaporation of the solvent under reduced pressure gave a colourless liquid (1.6 g) which was chromatographed on silica gel (150 g). Elution with ethyl acetate/petroleum ether (b.p. 60°–80°) (1:19) and evaporation of solvent afforded the title compound as a colourless liquid (0.8 g) b.p. 210°/0.01 mm Hg.

EXAMPLE 31

(1α,2α,4α,6α)-3-Oxatricyclo[4.2.0.0$^{2,4}$]octan-7-one

Sodium (2.1 g) was dissolved in methanol (50 ml) and the resultant solution added dropwise at 0° to a stirred solution of (1α,2α,3β,5α)-2-bromo-3-hydroxybicyclo[3.2.0]heptan-6-one (1.0 g) in methanol (15 ml). The mixture obtained was stirred at 0° for 15 min then at 20° for 45 min. Water (50 ml) was added and the mixture obtained was then extracted with chloroform (3×50 ml). The organic extracts were dried (MgSO$_4$) and evaporated and the residue purified by bulb-to-bulb distillation at 65°/0.005 torr to give the title compound as a colourless oil (0.58 g).

$\nu_{max}$ (liquid film) 1780 cm$^{-1}$.

$\tau$(CDCl$_3$ solution) 6.4 (3H, complex), 7.1 (2H, complex), 7.65 (1H, doublet, C-5β proton), 8.15 (1H, doublet of doublets, C-5α proton).

What is claimed is:

1. The compound of formula I,

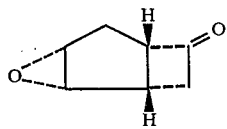

(I)

and derivatives thereof in which the ketone group is protected.

2. A compound as claimed in claim 1 having the formula II,

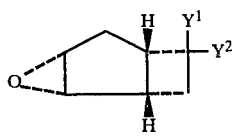

(II)

wherein $Y^1$ and $Y^2$ together represent a protected keto group.

3. A compound as claimed in claim 2 wherein $Y^1$ and $Y^2$ together represent a cyclic or acyclic ketal or thio ketal group.

4. A compound as claimed in claim 3 wherein $Y^1$ and $Y^2$ together represent a group $—A—R^1—A—$ where A represents an oxygen or sulphur atom and $R^1$ represents a $C_{2-6}$ alkylene group.

5. A compound as claimed in claim 4 wherein $R^1$ contains from 2 to 4 carbon atoms.

6. A compound as claimed in claim 4 wherein $Y^1$ and $Y^2$ together represent a 1,3-dioxolan ring.

7. A compond as claimed in claim 4 wherein $Y^1$ and $Y^2$ together represent a 1,3-dioxan or 1,3-dithian ring.

8. A compound as claimed in claim 3 wherein $Y^1$ and $Y^2$, which may be the same or different, each represents a group $—AR^2$ where A is an oxygen or sulphur atom and $R^2$ represents a $C_{1-6}$ alkyl group.

9. A compound as claimed in claim 8 wherein $Y^1$ and $Y^2$ are the same and represent methoxy or butoxy groups.

* * * * *